United States Patent [19]

Weber et al.

[11] 4,212,940
[45] Jul. 15, 1980

[54] PROCESS FOR THE PREPARATION OF 21-HYDROXY-20-METHYLPREGNANE DERIVATIVES

[75] Inventors: Alfred Weber; Mario Kennecke; Rudolf Müller, all of Berlin, Fed. Rep. of Germany

[73] Assignee: Schering Aktiengesellschaft, Berlin and Bergkamen, Fed. Rep. of Germany

[21] Appl. No.: 970,885

[22] Filed: Dec. 19, 1978

[51] Int. Cl.$^2$ .............................................. C07B 29/02
[52] U.S. Cl. .................................... 435/55; 435/863
[58] Field of Search ....................................... 195/51 G

[56] References Cited

U.S. PATENT DOCUMENTS

| 3,684,656 | 8/1972 | Waard | 195/51 G |
| 4,100,026 | 7/1978 | Weber et al. | 195/51 G |

Primary Examiner—Alvin E. Tanenholtz
Attorney, Agent, or Firm—Millen & White

[57] ABSTRACT

In a process for preparing 21-hydroxy-20-methylpregnane derivatives by fermenting a zoosterol or a phytosterol with a culture of Mycobacterium spec. NRRL B-3683 or NRRL B-3805 or a variant or mutant thereof, an improvement comprises conducting the fermentation at a pH value of 6.0–8.0 in the presence of an amount of borate ions or an organic boron compound effective to increase the yield of the 21-hydroxy-20-methylpregnane derivatives produced.

10 Claims, No Drawings

PROCESS FOR THE PREPARATION OF 21-HYDROXY-20-METHYLPREGNANE DERIVATIVES

BACKGROUND OF THE INVENTION

The present invention relates to a fermentative process for preparing 21-hydroxy-20-methylpregnane derivatives.

It is known that cultures of Mycobacterium spec. NRRL B-3683 and NRRL B-3805 can form 21-hydrox-20-methylpregnane derivatives of formula I as defined below, from zoosterols or phytosterols (Applied Microbiology 23 [1972]: 72 et seq. and Applied and Environmental Microbiology 32 [1976]: 310 et seq.). However, these compounds are formed only in trace amounts or in very small yields, so that the conventional process is hardly useful on a technical, industrial scale.

SUMMARY OF THE INVENTION

Accordingly, it is an object of the present invention to provide a process for producing 21-hydroxy-20-methylpregnane derivatives in significantly higher yields than those attainable using the above-mentioned conventional process.

Upon further study of the specification and appended claims, further objects and advantages of this invention will become apparent to those skilled in the art.

These objects have been achieved by providing in a process for preparing 21-hydroxy-20-methylpregnane derivatives by fermenting a zoosterol or a phytosterol with a culture of Mycobacterium spec. NRRL B-3683 or NRRL B-3805 or a variant or mutant thereof, the improvement which comprises conducting the fermentation at a pH value of 6.0–8.0 in the presence of an amount of borate ions or an organic boron compound effective to increase the yield of the 21-hydroxy-20-methylpregnane derivatives produced.

Preferred such products have the formula (I)

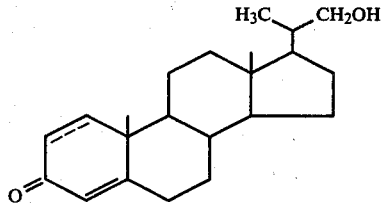

wherein ══ represents a single or double bond.

DETAILED DISCUSSION

The zoosterols and phytosterols suitable for use in this invention have the fully conventional structures known for such sterol substrates (e.g., see L. F. Fieser and M. Fieser: Steroids (Reinhold Publishing Corp., New York,) 1959, Chapter 11 and Rompps Chemie-Lexikon VII Edd. (Frankh'sche Verlagsh.Stuttgart) 1975 3334.

Preferred zoosterols or phytosterols have the formula II

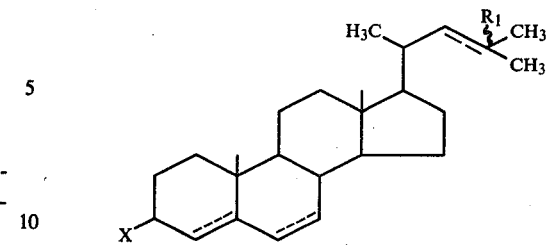

wherein
══ represents a single or a double bond;
X represents an oxo group or a hydrogen atom; and
$R_1$ is hydrogen, methyl or ethyl. Such starting materials are known. Of course, only one of $\Delta^4$ or $\Delta^5$ can exist in the same molecule.

Suitable zoosterols or phytosterols for use in the fermentation of this invention include, for example, cholesterol, stigmasterol, campesterol and brassicasterol; the sitosterols thereof, 3-acyl compounds thereof—such as, for example, the acetates of these sterols—, or the 3-keto-$\Delta^4$-steroids obtained from these sterols by Oppenauer oxidation, e.g., 4-cholesten-3-one, 4-stigmasten-3-one, 4-sitosten-3-one and 4-campesten-3-one.

According to this invention, the fermentation is conducted in the presence of borate ions or organic boron compounds or mixtures thereof.

When borate ions are used in accordance with this invention, the nature of the compound which provides the borate ions is not critical as long as it is otherwise compatible with the process of this invention. Typically, there can be used: a boric acid such as boric acid, orthoboric acid, metaboric acid or polyboric acid; as well as salts thereof such as the alkali or alkaline earth metal salts thereof, such as, sodium metaborate, disodium tetraborate, calcium metaborate, etc.

Suitable organic boron compounds include triphenyl borate. Organic boron compounds which are equivalent to the preferred triphenylborate include trialkylborates of the general formula $$B(OR_2)_3$$

wherein
$R_2$ represents identical alkyl groups of 1 to 6 carbon atoms e.g. trimethylborate, triethylborate, tripropylborate, triisopropylborate and tributylborate.

The fermenation, of course, must be conducted in the presence of sufficient borate ion or organic boron compund to effect an increase in yield over that obtained when no such reagents are utilized. It is preferably conducted in the presence of 1–5 g, preferably 1,5–3,0 g of agent(s) yielding borate ions per one liter of Mycobacterium spec. culture. These agents are preferably added 10–30 hours after the beginning of the fermentation. When employing an organic boron compound, 1–5 g, preferably 1–3 g, of the agent should be used on the same basis as given above. These agents also should be added 10–30 hours after the start of the fermentation.

When adding the agents which release borate ions, care must be taken that the pH value of the fermentation culture is conventionally adjusted to a value of between 6.0 and 8.0, preferably 6–7. For example, the conventional buffer systems utilized in the Examples of this application may be employed, but any system compatible pH adjustment technique may be employed. The same pH conditions must be met when the organic boron compounds are employed.

Unless otherwise specified herein, the fermentation is conducted under the conventional conditions disclosed, e.g., in the references cited in the Background of the Invention. The microorganisms are cultivated in a suitable conventional nutrient medium under aeration conditions to produce submerged cultures. Then, the substrate (dissolved in a suitable solvent or, preferably, in emulsified form) is added to the cultures. The fermentation is conducted until a maximum substrate conversion has been attained (about 96–160 hours). Generally, the process temperature is 25°–40° C.

Suitable substrate solvents include, for example, methanol, ethanol, glycol monomethyl ether, dimethylformamide and dimethylsulfoxide. The substrate can be emulsified, for example, by introducing the substrate through nozzles in micronized form; or dissolved in a water-miscible solvent (such as methanol, ethanol, acetone, glycol monomethyl ether, dimethylformamide or dimethyl sulfoxide) under strong turbulence conditions into water (preferably demineralized). The latter contains conventional emulsifiers. Suitable such emulsifiers include nonionic emulsifiers, such as, for example, ethylene oxide adducts or fatty acid esters of polyglycols. Examples of suitable emulsifiers are the commercial surfactants "Tegin," "Tagat," "Tween," and "Span."

During the fermentation, the emulsification of the substrates frequently causes an increased substrate throughput and, consequently, an increase in the substrate concentration. However, it is likewise possible, of course, to employ in the process of this invention other methods for raising the substrate throughput. These are well-known to those skilled in the art of fermentation.

The optimum substrate concentration in the solvent or emulsion as well as in the fermentation broth, the time at which the substrate is added, the duration of the fermentation and other relative proportions of fermentation components are dependent on the structure of the substrate employed. These variables must be determined, as generally required in microbiological steroid conversions, in each individual case by preliminary experiments, as is well known to persons skilled in the art. Typical such values are given in the Examples as well as in the above-cited references, where appropriate.

Generally, the yields obtained by using the process of this invention are in the range of 15–50% per weight.

An additional increase in yield of process products can be obtained if the Mycobacterium species are selected or mutated in the usual manner. Thus, it is possible, for example, to spread Mycobacterium spec. NRRL B-3805—suitably after treatment with mutagens—on blood-agar plates, thus obtaining individual colonies of a varying morphological appearance. If these individual colonies are isolated and tested for their capability of forming 21-hydroxy-20-methylpregnane derivatives, e.g., of formula I, it is found that there are often strains, especially among the selected strains which form round colonies, which provide a yield of 21-hydroxy-20-methylpregnane derivatives which is 1.5 to 3 times higher than the non-selective strain.

The 21-hydroxy-20-methylpregnane derivatives are valuable intermediates for the synthesis of pharmacologically effective steroids. Thus, it is possible, for example, to conventionally oxidize the compounds of formula I to the corresponding pregnane-20-carboxylic acids of formula III, which can be converted into the corresponding pregnane-3,20-dione derivatives of formula IV in accordance with the process described by H. Ruschig et al, (Chem. Ber. [Chemical Reports] 88. 1955: 883 et seq.).

Variants or mutants of Mycobacterium spec. NRRL B 3683 and NRRL B 3805 ca be prepared by the method described in the German published patent application No. 27 46 383.

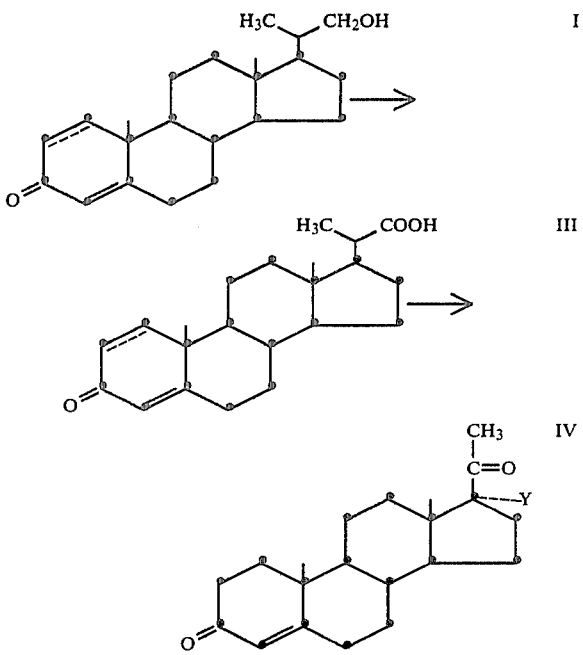

Y=(hydrogen or 17α-hydroxy)

The thus-obtained compounds are distinguished, as is known, by their progestational efficacy and are moreover valuable intermediates for the synthesis of numerous pharmacologically effective steroids.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

(a) A 2-liter Erlenmeyer flask with 500 ml. of a sterile nutrient medium containing
1% yeast extract
0.45% disodium hydrogen phosphate
0.34% potassium dihydrogen phosphate
0.2% "Tagat" 02
—adjusted to pH 6.7—
is inoculated with a supernatant broth of a dry culture of Mycobacterium spec. NRRL B-3805 and shaken for 3 days at 30° C. with 190 r.p.m.

(b) 22 g. of sitosterol is emulsified with 4.4 g. of "Tegin" and 430 ml. of water at 95° C. in an "Ultra-Turrax" mixer (Jahnke and Kunkel) for 25 minutes and thereafter filled up with water to 513 g. The emulsion is sterilized for 20 minutes at 120° C.

(c) A 500-ml. Erlenmeyer flask with 65 ml. of a sterile nutrient medium containing 2 g. corn steep liquor
0.3 g. diammonium hydrogen phosphate
0.25 g. "Tagat" 02
—adjusted to pH 6.5— is inoculated with 5 ml. of the Mycobacterium spec. germination culture. Then, 28 ml. of the suspension prepared as described in 1(b) (corresponding to 1.2 g. of sitosterol) is added thereto and, after 24 hours, 4 ml. of 4% aqueous sodium tetraborate solution is further added thereto, and the mixture is fermented for another 120 hours at 30° C. under shaking.

After the fermentation has taken place, the culture broth is extracted twice with respectively 100 ml. of ethylene chloride. The combined ethylene chloride extracts are thereafter combined with 11 g. of activated carbon and filtered through a folded filter. The filtrate is then concentrated at 40° C. with the use of a forced circulation evaporator and chromatographed on aluminum oxide. After the chromatography has been conducted, 135 mg. of 21-hydroxy-20-methyl-4-pregnen-3-one is obtained, m.p. 140°–141° C. (from ethyl acetate).

If the reaction is carried out under identical conditions, but without addding sodium tetraborate solution, 45 mg. of 21-hydroxy-20-methyl-4-pregnen-3-one is produced.

EXAMPLE 2

(a) As described in Example 1(b), 513 g. of an emulsion is prepared from 22 g. of 4-cholesten-3-one.

(b) Under the conditions of Example 1(c), 70 ml. of a Mycobacterium spec. NRRL B-3805 culture is incubated, combined with 28 ml. of the 4-cholesten-3-one emulsion and, after 24 hours, with 4 ml. of 4% aqueous sodium tetraborate solution, and fermented for another 120 hours at 30° C. under shaking. The fermentation batch is worked up as set forth in Example 1(c), thus obtaining 95 mg. of 21-hydroxy-20-methyl-4-pregnen-3-one, m.p. 142°–144° C.

If the reaction is conducted under the same conditions, but without adding sodium tetraborate solution, 40 mg. of 21-hydroxy-20-methyl-4-pregnen-3-one is obtained.

EXAMPLE 3

28 ml. of the sitosterol emulsion prepared as described in Example 1(b) is fermented as set forth in Example 1(c) with 70 ml. of a Mycobacterium spec. NRRL B-3805 culture, adding in place of the aqueous sodium tetraborate solution 6 ml. of 4% calcium metaborate suspension in water.

After the fermentation batch has been worked up as described in Example 1(c), 120 mg. of 21-hydroxy-20-methyl-4-pregnen-3-one is obtained, m.p. 141°–143° C.

EXAMPLE 4

28 ml. of the sitosterol emulsion prepared as set forth in Example 1(b) is fermented as indicated in Example 1(c) with 70 ml. of a Mycobacterium spec. NRRL B-3805 culture, using in place of the aqueous sodium tetraborate solution an addition of 5 ml. of a 4% triphenylborate solution.

After the fermentation batch has been worked up as disclosed in Example 1(c), 125 mg. of 21-hydroxy-20-methyl-4-pregnen-3-one is obtained, m.p. 142°–143° C.

EXAMPLE 5

(a) Under the conditions of Example 1(a), a Mycobacterium spec. NRRL B-3683 culture is incubated.

(b) 65 ml. of the nutrient medium described in Example 1(c) are combined with 5 ml. of the Mycobacterium spec. NRRL B-3683 incubation culture. Then the culture is combined with 28 ml. of the sitosterol emulsion described in Example 1(b) and, after 24 hours, with 4 ml. of 4% sodium tetraborate solution, and the fermentation is continued for another 120 hours. The fermentation batch is worked up as described in Example 1(c), thus obtaining 90 mg. of 21-hydroxy-20-methyl-1,4-pregnadien-3-one, m.p. 180°–182° C. (from ethyl acetate-acetone).

EXAMPLE 6

40 ml. of an incubation culture of Mycobacterium spec. NRRL B-3805—prepared in accordance with Example 1(a)—is centrifuged at 4,000 r.p.m.

The thus-obtained mass of bacteria is then washed twice with a salt solution buffered to pH 6 and containing 0.5% sodium chloride, 0.012% magnesium sulfate (heptahydrate), and 1.36% potassium dihydrogen phosphate, then suspended in 40 ml. of this salt solution, and combined with 10 ml. of a 0.5% 1-methyl-3-nitro-1-nitrosoguanidine solution.

The bacterial suspension is incubated for 1 hour at 30° C.; the bacteria are separated by centrifuging, washed twice with the above-mentioned salt solution, and spread on blood-agar plates (manufactured by Oxoid Ltd., London). From the thus-formed individual colonies, those are in each case selected which form round colonies, and from these incubation cultures are respectively prepared as described in Example 1(a). The incubation colonies serve in each instance for conducting the fermentation described in Example 1(c), with the following result:

| Number of Selected Strains Tested | Yield of 21-Hydroxy-20-methyl-4-pregnen-3-one | |
|---|---|---|
| | Without Addition of Sodium Tetraborate | With Addition of Sodium Tetraborate |
| 19 | 0–200 mg | — |
| 8 | 201–400 mg | — |
| 94 | 401–600 mg | — |
| 35 | 601–800 mg | — |
| 7 | 801–1,000 mg | 1,550–2,100 mg |
| 0 | 1,001–1,020 mg | — |
| 6 | 1,021–1,040 mg | 1,900–3,000 mg |
| 1 | 1,041–1,060 mg (150 mg) | 2,900 mg |
| 0 | 1,061–1,080 mg | — |
| 1 | 1,081–2,000 mg (195 mg) | 3,450 mg |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for preparing 21-hydroxy-20-methyl-pregnane derivatives by fermenting a zoosterol or a phytosterol with a culture of Mycobacterium spec. NRRL B-3683 or NRRL B-3805 or a variant or mutant thereof, the improvement which comprises conducting the fermentation at a pH value of 6.0–8.0 in the presence of an amount of borate ions, triphenylborate or a trialkylborate of the formula $B(OR_2)_3$, wherein $R_2$ represents identical alkyl groups of 1–6 carbon atoms, effective to increase the yield of the 21-hydroxy-20-methylpregnane derivatives produced.

2. The process of claim 1, wherein the starting material zoosterol or a phytosterol is of the formula

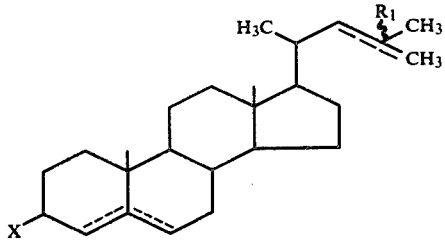

wherein

═ represents a single bond or a double bond;

X is an oxo group or a hydrogen atom; and $R_1$ is hydrogen, methyl or ethyl.

3. The process of claim 1 wherein the 21-hydroxy-20-methylpregnane produced is of the formula

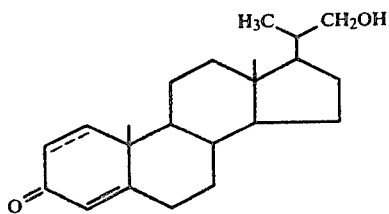

wherein

═ represents a single bond or a double bond.

4. The process of claim 2 wherein the 21-hydroxy-20-methylpregnane produced is of the formula

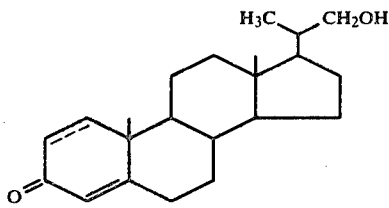

wherein

═ represents a single bond or a double bond.

5. The process of claim 1 wherein borate ions are provided by addition to the fermentation medium of orthoboric acid, metaboric acid or polyboric acid, or an alkali or alkaline earth metal salt thereof.

6. The process of claim 1, wherein 1–5 g of an agent yielding borate ions is employed per one liter of Mycobacterium spec. culture.

7. The process of claim 6, wherein the agent yielding borate ions is added 10–30 hours after the beginning of the fermentation.

8. The process of claim 1, wherein the Mycobacterium spec. is a variant or mutant of Mycobacterium spec. NRRL B-3683 or NRRL B-3805.

9. The process of claim 1, wherein the zoosterol or phytosterol is added to the fermentation medium as an emulsion.

10. The process of claim 1, wherein the fermentation is conducted in the presence of an amount of borate ions or triphenylborate effective to increase the yield of the 21-hydroxy-20-methylpregnane derivatives produced.

* * * * *

UNITED STATES PATENT AND TRADEMARK OFFICE
CERTIFICATE OF CORRECTION

PATENT NO. : 4,212,940
DATED : July 15, 1980
INVENTOR(S) : ALFRED WEBER et al

It is certified that error appears in the above-identified patent and that said Letters Patent are hereby corrected as shown below:

Cancel Formula of Claim 2. Replace with:

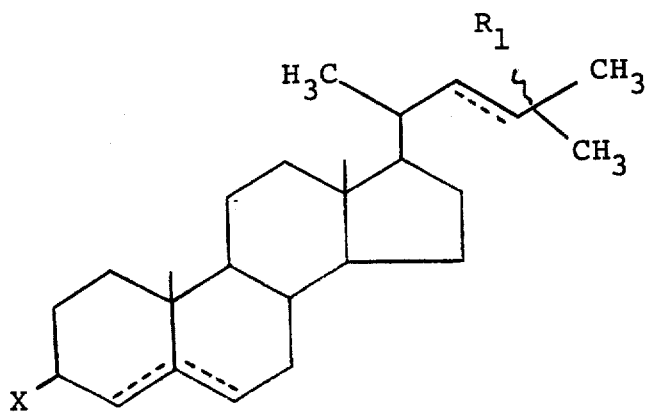

Signed and Sealed this

Thirtieth Day of September 1980

[SEAL]

Attest:

SIDNEY A. DIAMOND

Attesting Officer

Commissioner of Patents and Trademarks